(12) United States Patent
Kobayashi et al.

(10) Patent No.: US 11,541,033 B2
(45) Date of Patent: Jan. 3, 2023

(54) AGENT FOR PREVENTING OR TREATING ALZHEIMER'S DISEASE

(71) Applicant: FUJIFILM Toyama Chemical Co., Ltd., Tokyo (JP)

(72) Inventors: Hiroshi Kobayashi, Tokyo (JP); Yoshihiko Matsumoto, Tokyo (JP)

(73) Assignee: FUJIFILM Toyama Chemical Co., Ltd., Tokyo (JP)

(*) Notice: Subject to any disclaimer, the term of this patent is extended or adjusted under 35 U.S.C. 154(b) by 0 days.

(21) Appl. No.: 16/617,584

(22) PCT Filed: Jun. 1, 2018

(86) PCT No.: PCT/JP2018/021222
§ 371 (c)(1),
(2) Date: Nov. 27, 2019

(87) PCT Pub. No.: WO2018/221728
PCT Pub. Date: Dec. 6, 2018

(65) Prior Publication Data
US 2020/0108048 A1 Apr. 9, 2020

(30) Foreign Application Priority Data
Jun. 2, 2017 (JP) .............................. JP2017-109887

(51) Int. Cl.
*A61K 31/397* (2006.01)
*A61P 25/28* (2006.01)
*A61K 9/00* (2006.01)

(52) U.S. Cl.
CPC ............ *A61K 31/397* (2013.01); *A61P 25/28* (2018.01); *A61K 9/0053* (2013.01)

(58) Field of Classification Search
CPC ................................................... A61K 31/397
See application file for complete search history.

(56) References Cited

U.S. PATENT DOCUMENTS

| | | | |
|---|---|---|---|
| 6,489,481 B1 | 12/2002 | Keith et al. |
| 7,087,594 B2 | 8/2006 | Saitoh et al. |
| 8,119,625 B2 | 2/2012 | Iwakami et al. |
| 10,238,632 B2 | 3/2019 | Yano |
| 2005/0070521 A1 | 3/2005 | Saitoh et al. |
| 2005/0250843 A1 | 11/2005 | Nakada et al. |
| 2006/0194781 A1 | 8/2006 | Saitoh et al. |
| 2006/0205709 A1 | 9/2006 | Kimura et al. |
| 2009/0093453 A1 | 4/2009 | Iwakami et al. |
| 2011/0224180 A1 | 9/2011 | Pruss et al. |
| 2012/0028953 A1 | 2/2012 | Roughley et al. |
| 2015/0045345 A1 | 2/2015 | Inaba et al. |
| 2015/0166472 A1 | 6/2015 | Kim et al. |
| 2015/0203472 A1 | 7/2015 | Ceccarelli et al. |
| 2016/0324851 A1 | 11/2016 | Friedhoff et al. |
| 2017/0129915 A1 | 5/2017 | Tohda et al. |
| 2017/0165227 A1 | 6/2017 | Takahashi et al. |
| 2018/0153855 A1 | 6/2018 | Yano |
| 2018/0369194 A1 | 12/2018 | Kano et al. |
| 2020/0085787 A1 | 3/2020 | Kobayashi et al. |
| 2020/0155505 A1 | 5/2020 | Kobayashi et al. |
| 2020/0215030 A1 | 7/2020 | Kobayashi et al. |
| 2021/0137880 A1 | 5/2021 | Kobayashi et al. |
| 2021/0198245 A1 | 7/2021 | Yano et al. |

FOREIGN PATENT DOCUMENTS

| | | | |
|---|---|---|---|
| EP | 1 437 353 A1 | 7/2004 | |
| EP | 3 100 725 A1 | 12/2016 | |
| EP | 3 632 431 A1 | 4/2020 | |
| JP | 2002-528489 A | 9/2002 | |
| KR | 10-2008-0111131 A | 12/2008 | |
| RU | 2496784 C2 | 10/2013 | |
| RU | 2015112914 A | 11/2016 | |
| WO | 99/11293 A1 | 3/1999 | |
| WO | 03/035647 A1 | 5/2003 | |
| WO | 03/105830 A1 | 12/2003 | |
| WO | WO-03105830 A1 * | 12/2003 | ............ A61K 45/06 |
| WO | 2007/125913 A1 | 11/2007 | |
| WO | 2011-513374 A | 4/2011 | |
| WO | 2011/057199 A1 | 5/2011 | |
| WO | 2013/125617 A1 | 8/2013 | |
| WO | 2015/115582 A1 | 8/2015 | |
| WO | 2015/191506 A2 | 12/2015 | |
| WO | 2016/051799 A1 | 4/2016 | |
| WO | 2016/124508 A1 | 8/2016 | |
| WO | 2016/199878 A1 | 12/2016 | |
| WO | 2017/111005 A1 | 6/2017 | |

OTHER PUBLICATIONS

Takamura, Yusaku, et al. "Effects of the neurotrophic agent T-817MA on oligomeric amyloid-β-induced deficits in long-term potentiation in the hippocampal CA1 subfield." Neurobiology of Aging. (2014), vol. 35, pp. 532-536. (Year: 2014).*
Shigemon, Kenta, et al. "The factorial structure of the mini mental state examination (MMSE) in Japanese dementia patients." BMC Geriatrics. (2010), vol. 10, Issue 36, pp. 1 of 7 through 7 of 7. (Year: 2010).*
Coiovic, Mirjana B., et al. "Acetylcholinesterase Inhibitors: Pharmacology and Toxicology." Current Neuropharmacology. (2013), vol. 11, pp. 315-335. (Year: 2013).*
U.S. Appl. No. 16/617,660, Hiroshi Kobayashi, et al., filed Nov. 27, 2019, Pending.
Office Action dated Jun. 10, 2021 in U.S. Appl. No. 16/617,660.
Sarva et al., "Treatment Options in Degenerative Cerebellar Ataxia: A Systematic Review", Movement Disorders Clinical Practice, 2014, vol. 1, pp. 291-298.
Horig et al., "From bench to clinic and back: Perspective on the 1st IQPC Translational Research conference", Journal of Translational Medicine, 2004, vol. 2, No. 44, pp. 1-8.

(Continued)

Primary Examiner — John S Kenyon
(74) Attorney, Agent, or Firm — Sughrue Mion, PLLC

(57) ABSTRACT

An object of the present invention is to provide a drug which prevents progress of Alzheimer's disease and a method of preventing progress of Alzheimer's disease. Alzheimer's disease can be effectively prevented or treated by initiating administration of a pharmaceutical composition comprising 1-(3-(2-(1-benzothiophen-5-yl)ethoxy)propyl)azetidin-3-ol or a salt thereof as an active ingredient to a patient within a certain period from clinical diagnosis of Alzheimer's disease.

6 Claims, 2 Drawing Sheets

(56) References Cited

OTHER PUBLICATIONS

Schafer et al., "Failure is an option: learning from unsuccessful proof-of concept trials", Drug Discovery Today, 2008, Vo.. 13, pp. 913-916.
Decision under section 15 dated Mar. 22, 2021 issued in Indian patent application No. 201947049392.
Decision under section 15 dated Mar. 22, 2021 issued in Indian patent application No. 201947049390.
Office Action dated Jun. 1, 2021 issued in Singapore patent application No. 11201911512S, corresponding to U.S. Appl. No. 16/617,739.
Office Action dated Jun. 1, 2021 issued in Singapore patent application No. 11201911515Q.
Office Action dated Jun. 1, 2021 issued in Singapore patent application No. 11201911520U.
Office Action dated Jun. 1, 2021 issued in Singapore patent application No. 11201911519U.
Mascalchi et al., "Progression of Brain Atrophy in Spinocerebellar Ataxia Type 2: A Longitudinal Tensor-Based Morphometry Study", PLOS One, 2014, vol. 9, Issue 2, pp. 1-7, e89410.
Tosun et al., "Spatial patterns of brain amyloid-b burden and atrophy rate associations in mild cognitive impairment", Brain, 2011, vol. 134, pp. 1077-1088.
Hirata et al., "A Novel Neurotrophic Agent, T-817MA [1-{3-[2-(1-Benzothiopen-5-yl) Ethoxy] Propyl}-3-azetidinol Maleate], Attenuates Amyloid-$\beta$-Induced Neurotoxicity and Promotes Neurite Outgrowth in Rat Cultured Central Nervous System Neurons", The Journal of Pharmacology and Experimental Therapeutics, vol. 314, No. 1, pp. 252-259, 2005 (8 pages total).
Office Action dated May 29, 2020 in Russian Application No. 2019138538, corresponding to U.S. Appl. No. 16/617,607.
Uehara et al., "T-817MA, a novel neurotrophic agent, ameliorates loss of GABAergic parvalbumin-positive neurons and sensorimotor gating deficits in rats transiently exposed to MK-801 in the neonatal period", Journal of Psychiatric Research, vol. 46, No. 5, pp. 622-629, 2012 (8 pages total).
Office Action dated Apr. 27, 2020 from Russian Patent Office in Russian Application No. 2019138166/04, corresponding to U.S. Appl. No. 16/617,739.
Blennow, "Cerebrospinal Fluid Protein Biomarkers for Alzheimer's Disease", The American Society for Experimental NeuroTherapeutics, Apr. 2004, vol. 1, pp. 213-225 (13 pages total).
Office Action dated Jun. 25, 2021 in Korean Application No. 10-2019-7035347, corresponding to U.S. Appl. No. 16/617,739.
Office Action dated Jul. 2, 2021 in U.S. Appl. No. 16/617,552.
Office Action dated Jun. 10, 2021 in Russian U.S. Appl. No. 16/617,607, corresponding to U.S. Appl. No. 16/617,607.
Grigorenko et al., "Molecular Basics of Alzheimer's Disease", Molekulyarnaya Biologiya, 2007, vol. 41, No. 2, pp. 331-345 (15 pages total).
Lemere et al., "Sequence of Deposition of Heterogeneous Amyloid $\beta$-Peptides and APO E in Down Syndrome: Implications for Initial Events in Amyloid Plaque Formation", Neurobiology of Disease, 1996, vol. 3, No. 1, pp. 16-32, Article No. 0003 (17 pages total).
Office Action dated Jun. 10, 2021 in Mexican Application No. MX/a/2019/014306, corresponding to U.S. Appl. No. 16/617,607.
Office Action dated Jun. 24, 2021 in Korean Application No. 10-2019-7035349, corresponding to U.S. Appl. No. 16/617,552.
Office Action dated Jun. 24, 2021 in Korean Application No. 10-2019-7035350, corresponding to U.S. Appl. No. 16/617,607.
Office Action dated Jun. 25, 2021 in Korean Application No. 10-2019-7035348, corresponding to U.S. Appl. No. 16/617,660.
Manto et al., "Animal Models of Human Cerebellar Ataxias: a Cornerstone for the Therapies of the Twenty-First Century", Cerebellum, 2009, vol. 8, pp. 137-154 (18 pages total).
Office Action dated Jul. 13, 2021 in Japanese Application No. 2019-521350, corresponding to U.S. Appl. No. 16/617,552.
Shimohama et al., Journal of Japan Senile Medicine, vol. 50, No. 1, pp. 50:1-50:8, 2013 (8 pages total).
Office Action dated May 26, 2020 in Indian Application No. 201947049400.
International Search Report dated Jul. 24, 2018 in International Application No. PCT/JP2018/021225, corresponding to U.S. Appl. No. 16/617,552.
Written Opinion dated Jul. 24, 2018 in International Application No. PCT/JP2018/021225, corresponding to U.S. Appl. No. 16/617,552.
International Search Report dated Sep. 4, 2018 in corresponding International Application No. PCT/JP2018/021222.
Written Opinion dated Sep. 4, 2018 in corresponding International Application No. PCT/JP2018/021222.
International Search Report dated Jul. 24, 2018 in International Application No. PCT/JP2018/021223, corresponding to U.S. Appl. No. 16/617,739.
Written Opinion dated Jul. 24, 2018 in International Application No. PCT/JP2018/021223, corresponding to U.S. Appl. No. 16/617,739.
International Search Report dated Jul. 24, 2018 in International Application No. PCT/JP2018/021224, corresponding to U.S. Appl. No. 16/617,660.
Written Opinion dated Jul. 24, 2018 in International Application No. PCT/JP2018/021224, corresponding to U.S. Appl. No. 16/617,660.
International Search Report dated Jul. 24, 2018 in International Application No. PCT/JP2018/021226, corresponding to U.S. Appl. No. 16/617,607.
Written Opinion dated Jul. 24, 2018 in International Application No. PCT/JP2018/021226, corresponding to U.S. Appl. No. 16/617,607.
International Preliminary Report on Patentablity dated Dec. 3, 2019 in corresponding International Application No. PCT/JP2018/021222.
International Preliminary Report on Patentablity dated Dec. 3, 2019 in International Application No. PCT/JP2018/021223, corresponding to U.S. Appl. No. 16/617,739.
International Preliminary Report on Patentablity dated Dec. 3, 2019 in International Application No. PCT/JP2018/021224, corresponding to U.S. Appl. No. 16/617,660.
International Preliminary Report on Patentablity dated Dec. 3, 2019 in International Application No. PCT/JP2018/021225, corresponding to U.S. Appl. No. 16/617,552.
International Preliminary Report on Patentablity dated Dec. 3, 2019 in International Application No. PCT/JP2018/021226, corresponding to U.S. Appl. No. 16/617,607.
"2012 Alzheimer's Disease Facts and Figures", Alzheimer's Association, 2012 (72 pages total); http://www.alz.org/downloads/facts_figures_2012.pdf.
Sugimoto, "Development of Anti-Alzheimer's Disease Drug Based on Beta-Amyloid Hypothesis", Yakugaku Zasshi, 2010, vol. 130, No. 4, pp. 521-526 (6 pages total).
"Epidemiological studies on Alzheimer's disease in Japan", Japanese Journal of Clinical Medicine, 2008, vol. 66 (Extra ed. 1), pp. 23-27 (5 pages total).
Press Release by Seed Planning (Dec. 28, 2010) (3 pages total); http://www.seedplanning.co.jp/press/2010/2010122801.html.
Japanese Journal of Clinical Psychopharmacology, 2011, vol. 14, No. 7, pp. 1123-1129.
Japanese Journal of Clinical Psychopharmacology, 2012, vol. 15, No. 3, pp. 311-321.
Takamura et al., "Effects of the neurotrophic agent T-817MA on oligomeric amyloid-$\beta$-induced deficits in long-term potentiation in the hippocampal CA1 subfield", Neurobiology of Aging, 2014, vol. 35, pp. 532-536 (5 pages total).
Fujifilm Corp., "II stage clinical experiment in the United States for Alzheimer's dementia therapeutic drug 'T-817MA': drastically restricting, with statistical significant difference, progress of deterioration in cognitive function with respect to patient group having this innovative two effects of reducing phosphorylation tau in cerebrospinal fluid and restricting hippocampal atrophy in brain", News release, Jul. 19, 2017 (1 page total).
McKhann et al., "The diagnosis of dementia due to Alzheimer's disease: Recommendations from the National Institute on Aging-Alzheimer's Association workgroups on diagnostic guidelines for Alzheimer's disease", Alzheimer's Dement., May 2011, vol. 7, No. 3, pp. 263-269, (52 pages total).

(56) References Cited

OTHER PUBLICATIONS

Kimura et al., "T-817MA, a neurotrophic agent, ameliorates the deficits in adult neurogenesis and spatial memory in rats infused i.c.v. with amyloid-β peptide", British Journal of Pharmacology, 2009, vol. 157, pp. 451-463 (13 pages total).

Moreno et al., "Blocking effects of human tau on squid giant synapse transmission and its prevention by T-817MA", Frontiers in Synaptic Neuroscience, May 2011, vol. 3, Article 3, pp. 1-8 (8 pages total).

Fukushima et al., "T-817MA, a neuroprotective agent, attenuates the motor and cognitive impairments associated with neuronal degeneration in P301L tau transgenic mice", Biochemical and Biophysical Research Communications, 2011, vol. 407, pp. 730-734 (5 pages total).

Fukushima, "Pharmacological properties of T-817MA, a novel neurotrophic agent, for treatment of Alzheimer's disease", Folia Pharmacologica Japonica, 2010, vol. 136, pp. 11-14 (2 pages total). Proceedings of the Annual Meeting of the Japanese Research Group on Senile Dementia, 2010, vol. 15, pp. 79-81 (4 pages total).

Lo et al., "Longitudinal Change of Biomarkers in Cognitive Decline", Archives of Neurology, 2011, vol. 68, No. 10, pp. 1257-1266 (10 pages total).

Japanese Journal of Geriatrics, 2013, vol. 50, No. 1, pp. 1-8 (9 pages total).

Jack Jr. et al., "Tracking pathophysiological processes in Alzheimer's disease: an updated hypothetical model of dynamic biomarkers", Lancet Neurology, Feb. 2013, vol. 12, No. 2, pp. 207-216 (10 pages total).

Office Action dated Mar. 2, 2020 in Russian Application No. 2019138164, corresponding to U.S. Appl. No. 16/617,660.

Office Action dated Dec. 8, 2020, issued by the Korean Intellectual Property Office in Korean Application No. 10-2019-7035347, corresponding to U.S. Appl. No. 16/617,739.

Office Action dated Dec. 8, 2020, issued by the Korean Intellectual Property Office in Korean Application No. 10-2019-7035348, corresponding to U.S. Appl. No. 16/617,660.

Office Action dated Dec. 9, 2020, issued by the Korean Intellectual Property Office in Korean Application No. 10-2019-7035350, corresponding to U.S. Appl. No. 16/617,607.

Office Action dated Dec. 9, 2020, issued by the Korean Intellectual Property Office in Korean Application No. 10-2019-7035349, corresponding to U.S. Appl. No. 16/617,552.

Hearing Notice dated Jan. 8, 2021, issued by the Indian Intellectual Property Office in Indian Application No. 201947049401, corresponding to U.S. Appl. No. 16/617,739.

Office Action dated Jul. 21, 2021 in New Zealand Application No. 759585, corresponds to U.S. Appl. No. 16/617,739.

Office Action dated Jul. 21, 2021 in New Zealand Application No. 759647, corresponds to U.S. Appl. No. 16/617,660.

Office Action dated Jul. 21, 2021 in New Zealand Application No. 759657, corresponds to U.S. Appl. No. 16/617,552.

Office Action dated Jul. 22, 2021 in New Zealand Application No. 759662, corresponds to U.S. Appl. No. 16/617,607.

Hearing Notice dated Feb. 3, 2021 issued by the Indian Patent Office in Application No. 201947049390, corresponding to U.S. Appl. No. 16/617,607.

Hearing Notice dated Feb. 3, 2021 issued by the Indian Patent Office in Application No. 2019470479400, corresponding to U.S. Appl. No. 16/617,552.

Official Action dated Jan. 27, 2021 issued by the Canadian Patent Office in Application No. 3,067,453, corresponding to U.S. Appl. No. 16/617,739.

Office Action dated Jan. 27, 2021 issued by the Canadian Patent Office in Application No. 3,067,455, corresponding to U.S. Appl. No. 16/617,660.

Official Action dated Jan. 27, 2021 issued by the Canadian Patent Office in Application No. 3,067,456, corresponding to U.S. Appl. No. 16/617,552.

Official Action dated Jan. 29, 2021 issued by the Canadian Patent Office in Application No. 3,067,458, corresponding to U.S. Appl. No. 16/617,607.

Hearing Notice dated Jan. 8, 2021 issued by the Indian Patent Office in application No. 201947049392, corresponding to U.S. Appl. No. 16/617,660.

Office Action dated Jun. 23, 2021 in U.S. Appl. No. 16/617,739.

Jagust, "Is amyloid-ß hamifultothe brain? Insights from human imaging studies", Brain, 2016, vol. 139, pp. 23-30.

Healthline, "Brain Atrophy (Cerebral Atrophy)", updated Mar. 29, 2019 https://www.healthline.com/health/brain-atrophy (10 pages total).

Office Action dated Jun. 23, 2021 in U.S. Appl. No. 16/617,607.

Nguyen et al., "Ameliorative Effects of a Neuroprotective Agent, T-817MA, on Place Learning Deficits Induced by Continuous Infusion of Amyloid-B Peptide (1-40) in Rats", Hippocampus, 2007, vol. 17, pp. 443-455.

Tosun et al., "Relationship Between Regional Brain Amyloid-ß Deposition and Brain Atrophy Rates in Mild Cognitive Impairment", Alzheimer's & Dementia: The Journal of the Alzheimer's Association, Jul. 1, 2010, XP027440489, vol. 6, No. 4, p. e15 (total 1 page).

Extended European Search Report dated May 7, 2020 from European Patent Office in EP Application No. 18810520.9, corresponding to U.S. Appl. No. 16/617,739.

Schneider et al., "A Phase 2 Multicenter, Randomized, Placebo-Controlled Trial to Evaluate The Efficacy and Safety of Edonerpic (T-817) In Patients with Mild to Moderate Alzheimer's Disease", Alzheimer's & Dementia: The journal of the Alzheimer's Association, Jul. 19, 2017, P4-573. Vol. 13, No. 7, XP085218926, p. P1572 (total 1 page).

Yamaguchi et al., "T-817MA, a neurotrophic compound, reverses AB neurotoxicity and promotes neurite outgrowth through PI3-Kinase pathway in rat primary neurons", Abstract of the Annual Meeting of the Society for Neuroscience, Nov. 8, 2003, XP008135922, pp. 1-2 (total 2 pages).

Quinti et al., "A Novel Drug-Screening Platform in Microglial Cells Indentifies Potential AD Drugs", Alzheimer's & Dementia: The journal of the Alzheimer's Association, Jul. 19, 2017, XP085218817, P4-404, vol. 1, No. 13, p. P1485 (total 1 page).

Yano et al., "SIGMA-1 Receptor is a Molecular Target for Novel Neuropretectant T-817MA", Alzheimer's & Dementia: The Journal of the Alzheimer's Association, Jul. 1, 2015, XP029355158, P4-210, vol. 11, No. 7, p. P861 (total 1 page).

Nakagawa et al., "T-817MA, A Newly Developing Anti-Alzheimer's Agent, Protects Neurons and Recovers Memory Impairment in Amyloid B-Infused Rats and P301L Taumutated Mice", Alzheimer's & Dementia: The Journal of the Alzheimer's Association, Jul. 1, 2005, XP027823394, P-193, vol. 1, No. 1, p. S69-S70 (total 2 pages).

Extended European Search Report dated May 11, 2020 from European Patent Office in EP Application No. 18810759.3, corresponding to the present application.

Office Action dated Aug. 10, 2020 in Australian Application No. 2018276638, subject matter-related to U.S. Appl. No. 16/617,552.

Office Action dated Aug. 14, 2020 in Australian Application No. 2018277981, subject matter-related to U.S. Appl. No. 16/617,552.

Office Action dated Aug. 17, 2020 in Australian Application No. 2018277983, subject matter-related to U.S. Appl. No. 16/617,552.

Office Action dated Aug. 21, 2020 in Australian Application No. 2018277982, subject matter-related to U.S. Appl. No. 16/617,552.

Office Action dated Jul. 3, 2020 in Russian Application No. 2019138699, corresponding to U.S. Appl. No. 16/617,552.

Office Action dated Feb. 17, 2021, issued in Russian Application No. 2019138166/04, corresponding to U.S. Appl. No. 16/617,739.

Decision under section 15 dated Feb. 23, 2021, issued in Indian Application No. 201947049401, corresponding to U.S. Appl. No. 16/617,739.

Grimmer et al., "Beta Amyloid in Alzheimer's Disease: Increased Deposition in Brain Is Reflected in Reduced Concentration in Cerebrospinal Fluid", Biol. Psychiatry, 2009, vol. 65, No. 11, pp. 927-934 (17 pages total).

(56) References Cited

OTHER PUBLICATIONS

Kolobov et al., "Modern Pharmacological Models of Alzheimer's Disease", Original Articles, Experimental Neurology, 2014, vol. 8, No. 3, pp. 38-44 (32 pages total).
Office Action dated Oct. 23, 2020 in Russian Application No. 2019138538, corresponding to U.S. Appl. No. 16/617,607.
Office Action dated Sep. 25, 2020 in Russian Application No. 2019138166, corresponding to U.S. Appl. No. 16/617,739.
Extended European Search Report dated May 11, 2020 in European Application No. 18809579.8, corresponding to U.S. Appl. No. 16/617,552.
Extended European Search Report dated May 11, 2020 in European Application No. 18809739.8, corresponding to U.S. Appl. No. 16/617,660.
Extended European Search Report dated May 13, 2020 in European Application No. 18809110.2, corresponding to U.S. Appl. No. 16/617,607.
Office Action dated May 26, 2020 in Indian Application No. 201947049390, corresponding to U.S. Appl. No. 16/617,607.
Office Action dated May 26, 2020 in Indian Application No. 201947049392, corresponding to U.S. Appl. No. 16/617,660.
Office Action dated May 26, 2020 in Indian Application No. 201947049401, corresponding to U.S. Appl. No. 16/617,739.
Kawasaki et al., "A Neuroprotective Agent, T-817MA (1-{3-[2-(1-benzothiophen-5-yl)ethoxy]propyl}azetidin-3-ol Maleate), Prevents 1-methyl-4-phenyl-1,2,3,6-tetrahydropyridine-induced Neurotoxicity in Mice", Neuropharmacology, vol. 55, Issue 5, Oct. 2008, pp. 654-660, Abstract only.
Office Action dated Nov. 9, 2021 in U.S. Appl. No. 16/617,607.
Restriction Requirement dated Jun. 3, 2021 in U.S. Appl. No. 16/760,512.
Office Action dated Aug. 18, 2021 in U.S. Appl. No. 16/760,512.
Marquer et al., "Increasing membrane cholesterol of neurons in culture recapitulates Alzheimer's disease early phenotypes", Molecular Neurodegeneration, 2014, vol. 9, No. 60, pp. 1-13 (13 pages total).
Chemical Abstracts Registry No. 519187-30-5, Indexed in the Registry file on STN CAS Online, May 23, 2003 (1 page total).
Bae et al., "Cholesterol biosynthesis from lanosterol: molecular cloning, chromosomal localization, functional expression and liver-specific gene regulation of rat sterol $\Delta^8$-isomerase, a cholesterogenic enzyme with multiple functions", Biochem. J., 2001, vol. 353, pp. 689-699 (11 pages total).
Berardi et al., "Novel 4-(4-Aryl)cyclohexyl-1-(2-pyridyl)piperazines as $\Delta_8$-$\Delta_7$ Sterol Isomerase (Emopamil Binding Protein) Selective Ligands with Antiproliferative Activity", J. Med. Chem., 2008, vol. 51, No. 23, pp. 7523-7531 (9 pages total).
Communication dated Jul. 3, 2020, from the European Patent Office in application No. 18873445.3, corresponds to U.S. Appl. No. 16/760,512.
Derry et al., "Mutations in a $\Delta^8$-$\Delta^7$ sterol isomerase in the tattered mouse and X-linked dominant chondrodysplasia punctata", Nature Genetics, Jul. 1999, vol. 22, pp. 286-290 (5 pages total).
International Preliminary Report on Patentability dated May 5, 2020, issued by the International Bureau in application No. PCT/JP2018/040283, corresponds to U.S. Appl. No. 16/760,512.
International Search Report dated Jan. 29, 2019, issued by the International Searching Authority in application No. PCT/JP2018/040283, corresponds to U.S. Appl. No. 16/760,512.
Laggner et al., "Discovery of High-Affinity Ligands of G Receptor, ERG2, and Emopamil Binding Protein by Pharmacophore Modeling and Virtual Screening", J. Med. Chem., 2005, vol. 48, No. 15, pp. 4754-4764 (11 pages total).
Moebius et al., "Identification of a 27-kDa High Affinity Phenylalkylamine-Binding Polypeptide as the $\sigma_1$ Binding Site by Photoaffinity Labeling and Ligand-Directed Antibodies", Molecular Pharmacology, 1993, vol. 44, pp. 966-971 (8 pages total).
Silve et al., "Emopamil-binding Protein, a Mammalian Protein That Binds a Series of Structurally Diverse Neuroprotective Agents, Exhibits $\Delta 8$-$\Delta 7$ Sterol Isomerase Activity in Yeast", The Journal of Biological Chemistry, Sep. 13, 1996, vol. 271, No. 37, pp. 22434-22440 (8 pages total).
Written Opinion dated Jan. 29, 2019, issued by the International Searching Authority in application No. PCT/JP2018/040283, corresponds to U.S. Appl. No. 16/760,512.
Office Action dated Nov. 4, 2021 in Mexican Application No. MX/a/2019/014306, corresponds to U.S. Appl. No. 16/617,607.
Notice of Allowance dated Sep. 28, 2021 in U.S. Appl. No. 16/617,660.
Communication dated Aug. 4, 2021 from the Canadian Patent Office in Canadian Application No. 3,067,456, corresponds to U.S. Appl. No. 16/617,552.
Communication dated Aug. 11, 2021 from the Canadian Patent Office in Canadian Application No. 3,067,458, corresponds to U.S. Appl. No. 16/617,607.
Communication dated Aug. 17, 2021 from the Mexican Patent Office in Mexican Application No. MX/a/2019/014306, corresponds to U.S. Appl. No. 16/617,607.
Notice of Final Rejection dated Aug. 24, 2021 from the Korean Patent Office in Korean Application No. 10-2019-7035348, corresponds to U.S. Appl. No. 16/617,660.
SIM integrated internal medicine understood through anatomy and pathophysiology 10 : Neurology Spinocerebellar Degeneration, May 30, 2013 (12 pages total).
Busciglio et al., "Altered Metabolism of the Amyloid β Precursor Protein Is Associated with Mitochondrial Dysfunction in Down's Syndrome", Neuron, 2002, vol. 33, pp. 677-688 (12 pages total).
Chetelat et al., "Relationship between Atrophy and β-Amyloid Deposition in Alzheimer Disease", Ann Neurol, 2010, vol. 67, pp. 317-324 (8 pages total).
Office Action dated Dec. 14, 2021 in Korean Application No. 10-2019-7035349, corresponds to U.S. Appl. No. 16/617,552.
Office Action dated Dec. 14, 2021 in Korean Application No. 10-2019-7035350, corresponds to U.S. Appl. No. 16/617,607.
Office Action dated Dec. 20, 2021 in Korean Application No. 10-2019-7035347, corresponds to U.S. Appl. No. 16/617,739.
Office Action dated Dec. 9, 2021 in Mexican Application No. MX/a/2019/014300, corresponding to U.S. Appl. No. 16/617,552.
U.S. Appl. No. 16/617,739, Hiroshi Kobayashi, et al., filed Nov. 27, 2019, Pending.
U.S. Appl. No. 16/617,660, Hiroshi Kobayashi, et al., filed Nov. 27, 2019, Allowed.
U.S. Appl. No. 16/617,552, Hiroshi Kobayashi, et al., filed Nov. 27, 2019, Pending.
U.S. Appl. No. 16/617,607, Hiroshi Kobayashi, et al., filed Nov. 27, 2019, Pending.
U.S. Appl. No. 16/760,512, Takeaki Yano, et al., filed Apr. 30, 2020, Pending.
Decision of Refusal dated Nov. 30, 2021 from the Japanese Patent Office in Japanese Application No. 2019-521350, corresponds to U.S. Appl. No. 16/617,552.
A. Sugiyama and H. Shimada, "Tau PET Imaging for Dementia in Clinical Practice", Radioisotopes, vol. 65, No. 12, pp. 517-522 (Japan Radioisotope Association, 2016) (6 pages total).
Naoji Amano, "Neurodegenerative Diseases and Tauopathy", Shinshu Journal, 2002, vol. 50, No. 3, pp. 113-120 (8 pages total).
Y. Soeda and A. Takashima, "Development of disease modifying drugs for dementia—focusing on anti-tau drugs", Clinical Neurology, vol. 54, pp. 1178-1180 (2014) (3 pages total).
Y. Yoshiyama, Nippon Rinsho, Japanese Journal of Clinical Medicine, vol. 69, Suppl. 8, pp. 262-266 (2011) (5 pages total).
H. Takahashi, "Animal models of Alzheimer's disease for preclinical research", Folia Pharmacol. Jpn., vol. 136, No. 1, pp. 6-10 (2010) (5 pages total).
"Guidance for Industry: Estimating the Maximum Safe Starting Dose in Initial Clinical Trials for Therapeutics in Adult Healthy Volunteers", U.S. Department of Health and Human Services, Food and Drug Administration, Center for Drug Evaluation and Research (CDER), Pharma and Toxicology, 2005, pp. 1-27 (30 pages total).
Final Office Action dated Dec. 8, 2021 in U.S. Appl. No. 16/760,512.
Office Action dated Dec. 15, 2021 in U.S. Appl. No. 16/617,739.

(56) References Cited

OTHER PUBLICATIONS

Notice of Allowance dated Dec. 15, 2021 in U.S. Appl. No. 16/617,660.
Aisen et al., "On the path to 2025: understanding the Alzheimer's disease continuum", Alzheimer's Research & Therapy, 2017, vol. 9, No. 60, pp. 1-10 (10 pages total).
Head et al., "Alzheimer's Disease in Down Syndrome", Eur J Neurodegener Dis., 2012, vol. 1, No. 3, pp. 353-364 (16 pages total).
Office Action dated Feb. 14, 2022 in U.S. Appl. No. 16/617,607.
Office Action dated Jan. 25, 2022 in Russian Application No. 2019138538, corresponds to U.S. Appl. No. 16/617,607.
Office Action dated Jan. 28, 2022 in U.S. Appl. No. 16/617,552.
Office Action dated Feb. 18, 2022 in Canadian Application No. 3,067,456, corresponds to U.S. Appl. No. 16/617,552.
Office Action dated Mar. 2, 2022 in Mexican Application No. MX/a/2019/014302, corresponds to U.S. Appl. No. 16/617,660.
Office Action dated Mar. 3, 2022 in Mexican Application No. MX/a/2019/014310, corresponds to U.S. Appl. No. 16/617,739.
Notice of Allowance dated Apr. 1, 2022 in U.S. Appl. No. 16/617,739.
Office Action dated Mar. 1, 2022 in Mexican Application No. MX/a/2019/014306, corresponds to U.S. Appl. No. 16/617,607.
Notice of Allowance dated Apr. 4, 2022 in U.S. Appl. No. 16/617,607.
Office Action dated Apr. 4, 2022 in New Zealand Application No. 759662, corresponds to U.S. Appl. No. 16/617,607.
Office Action dated Mar. 31, 2022 in Korean Application No. 10-2019-703530, corresponds to U.S. Appl. No. 16/617,607.
Communication dated Apr. 12, 2022 from the Korean Patent Office in Korean Application No. 10-2019-7035347, corresponds to U.S. Appl. No. 17/617,739.
Communication dated Apr. 7, 2022 from the Korean Patent Office in Korean Application No. 10-2019-7035349, corresponds to U.S. Appl. No. 16/617,552.
Office Action dated May 10, 2022 in corresponding Japanese Application No. 2019-521347.
Office Action dated May 6, 2022 in Chinese Application No. 201880035394.0, corresponds to U.S. Appl. No. 16/617,739.
Office Action dated May 6, 2022 in Chinese Application No. 201880035501.X, corresponds to U.S. Appl. No. 16/617,660.
Office Action dated May 6, 2022 in Chinese Application No. 201880035503.9, corresponds to U.S. Appl. No. 16/617,552.
Office Action dated May 6, 2022 in Chinese Application No. 201880035521.7, corresponds to U.S. Appl. No. 16/617,607.
Office Action dated May 10, 2022 in Japanese Application No. 2019-521348, corresponds to U.S. Appl. No. 16/617,739.
Reconsideration Report dated Apr. 28, 2022 in Japanese Application No. 2019-521350, corresponds to U.S. Appl. No. 16/617,552.
Office Action dated May 24, 2022 in Japanese Application No. 2019-521349, corresponds to U.S. Appl. No. 16/617,660.
Peng Ying et al., "Progress of clinical trials in Alzheimer's disease drugs", Acta Pharmaceutica Sinica, 2016, vol. 51, No. 8, pp. 1185-1195 (11 pages total).
Yuli Xie, Pharmaceutical and Clinical Research, 2011, vol. 19, No. 1, pp. 1-7 (7 pages total).
Buccarello et al., "Sex Impact on Tau-Aggregation and Postsynaptic Protein Levels in the P301L Mouse Model of Tauopathy" Journal of Alzheimer's Disease, 2017, vol. 56, No. 4, pp. 1279-1292 (27 pages total).
Zheng et al., "Amyloid β Peptide induces Tau Phosphorylation and Loss of Cholinergic Neurons in Rat Primary Septal Cultures", Neuroscience, 2002, vol. 115, No. 1, pp. 201-211 (11 pages total).
Office Action dated Jun. 6, 2022 in U.S. Appl. No. 16/617,552.
Office Action dated Jun. 7, 2022 in Japanese Application No. 2019-521351, corresponds to U.S. Appl. No. 16/617,607.
Office Action dated Apr. 12, 2022 in Israeli Application No. 270910, corresponds to U.S. Appl. No. 16/617,660.
Office Action dated Jul. 26, 2022 in Brazilian Application No. BR112019024834, corresponds to U.S. Appl. No. 16/617,607.
Office Action dated Aug. 15, 2022 in U.S. Appl. No. 16/617,739.
Office Action dated Aug. 16, 2022 in U.S. Appl. No. 16/617,607.
Office Action dated Jun. 26, 2022 in Israeli Application No. 270912, corresponds to U.S. Appl. No. 16/617,552.
Office Action dated Jun. 27, 2022 in Israeli Application No. 270922, corresponds to U.S. Appl. No. 16/617,739.
Office Action dated Aug. 29, 2022 in Korean Application No. 10-2022-7022765, corresponds to U.S. Appl. No. 16/617,552.
Office Action dated Aug. 29, 2022 in Korean Application No. 10-2022-7022766, corresponds to U.S. Appl. No. 16/617,552.
Office Action dated Sep. 13, 2022 in Brazilian Application No. BR112019024810, corresponds to U.S. Appl. No. 16/617,739.
Office Action dated Sep. 13, 2022 in Brazilian Application No. BR112019024811, corresponds to U.S. Appl. No. 16/617,660.
Office Action dated Oct. 18, 2022 by Japan Patent Office in Japanese Application No. 2019-550404, which corresponds to U.S. Appl. No. 16/760,512.
Hanney et al., "Memantine for dementia in adults older than 40 years with Down's syndrome (MEADOWS): a randomised, double-blind, placebo-controlled trial", Lancet, 2012, vol. 379, pp. 528-536 (9 pages total).
Livingstone et al., "Pharmacological interventions for cognitive decline in people with Down syndrome (Review)", Cochrane Database of Systematic Reviews, 2015, Issue 10, Art. No. CD011546 (57 pages total).
Office Action dated Nov. 8, 2022 in Japanese Application No. 2019-521351, corresponds to U.S. Appl. No. 16/617,607.
Office Action dated Nov. 15, 2022 in Japanese Application No. 2019-521347, corresponds to U.S. Appl. No. 16/617,584 (the present application).
Office Action dated Nov. 15, 2022 in Japanese Application No. 2019-521348, corresponds to U.S. Appl. No. 16/617,739.

\* cited by examiner

[Figure 1]
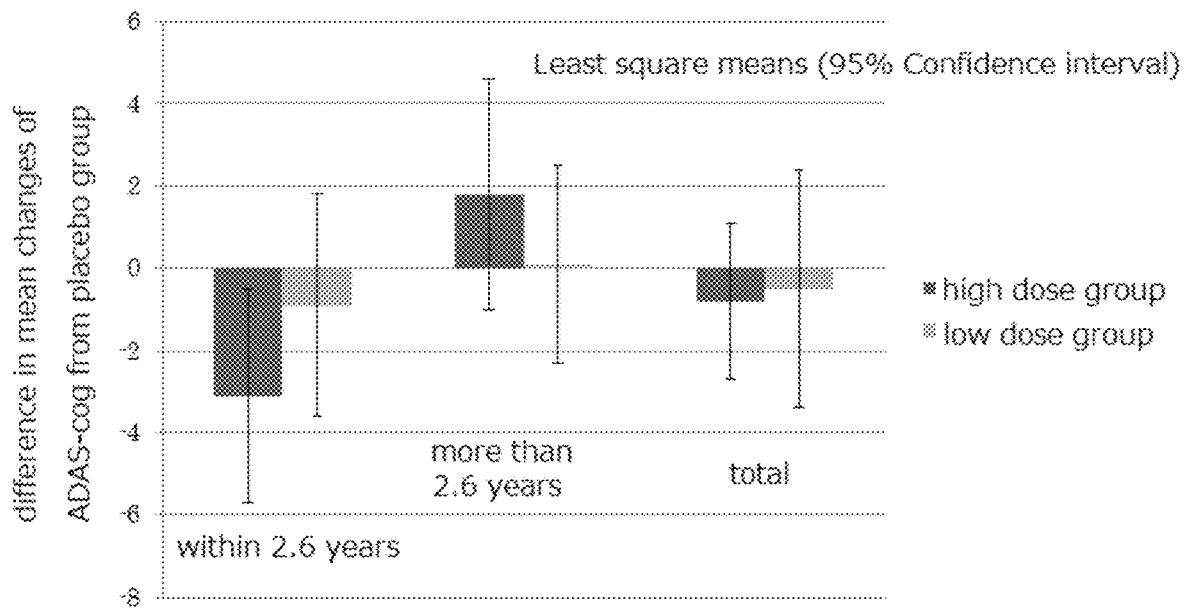
[Figure 2]
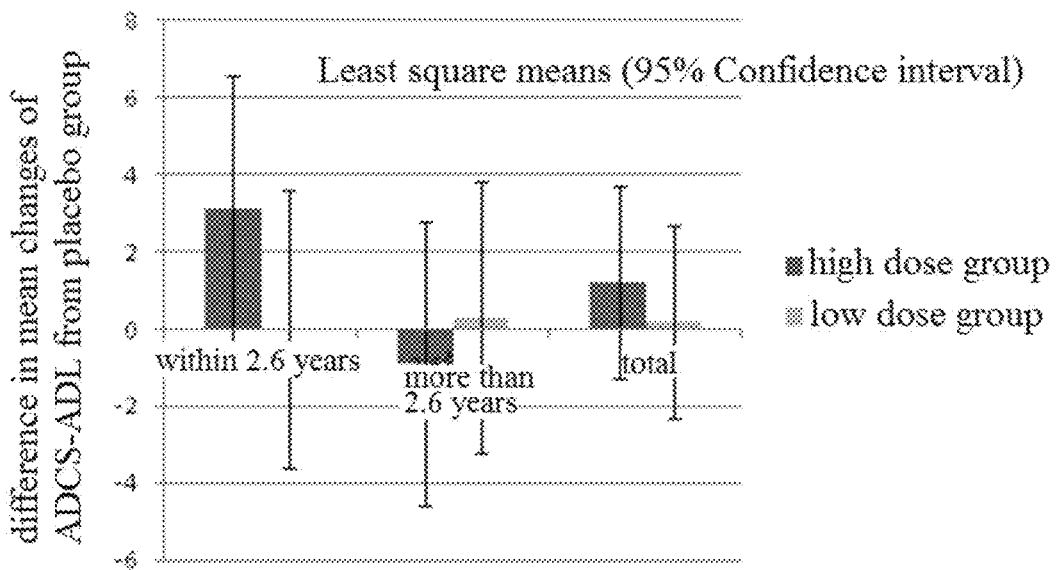

[Figure 3]
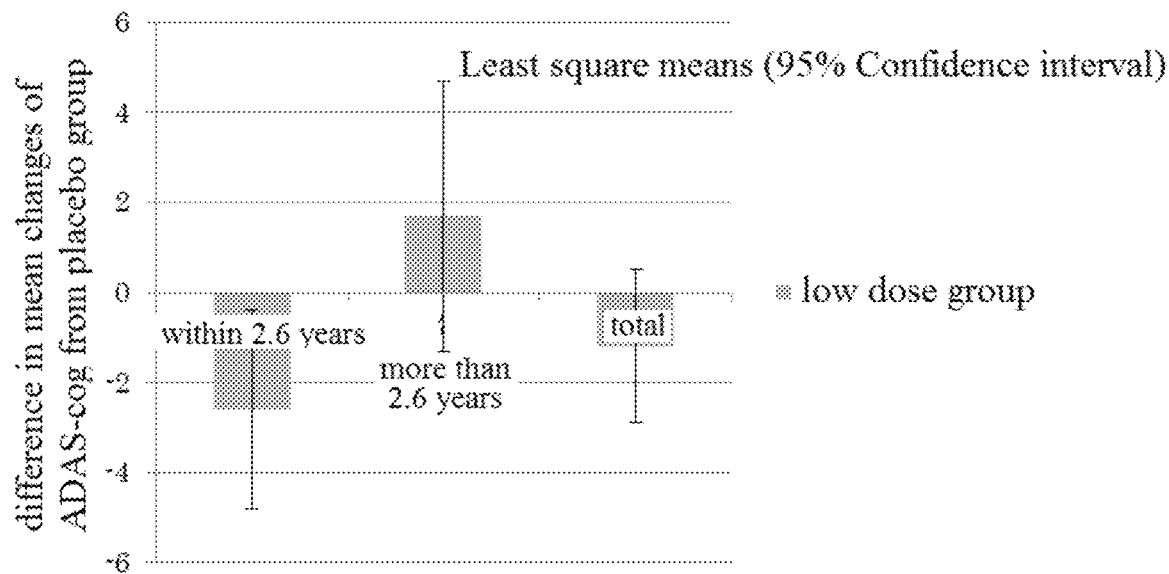
[Figure 4]
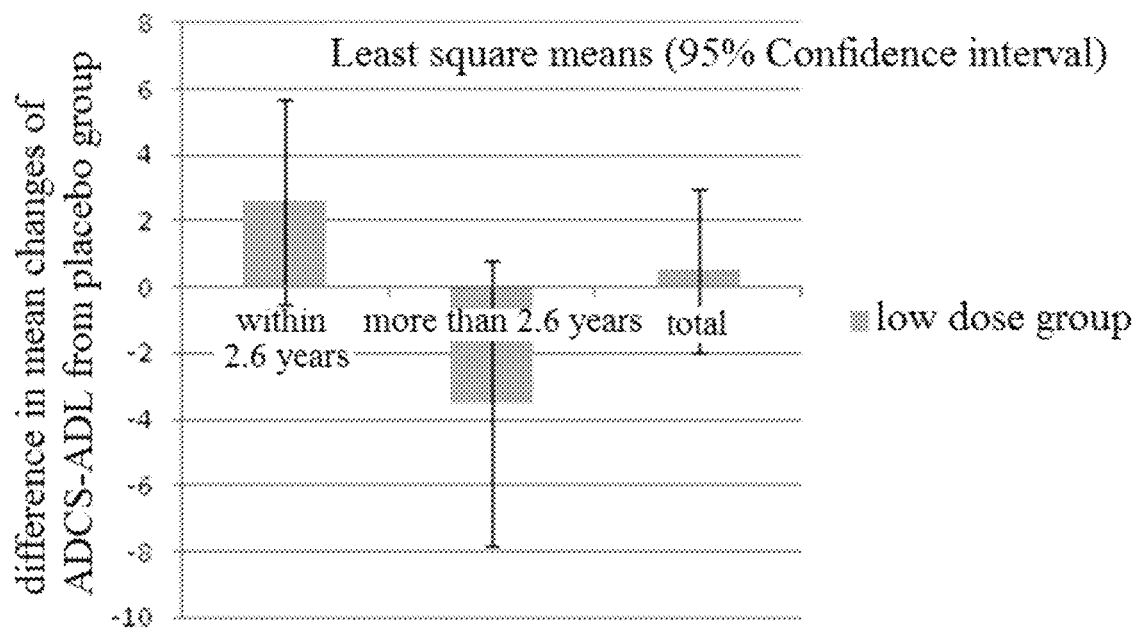

AGENT FOR PREVENTING OR TREATING ALZHEIMER'S DISEASE

CROSS REFERENCE TO RELATED APPLICATIONS

This application is a National Stage of International Application No. PCT/JP2018/021222, filed on Jun. 1, 2018, which claims priority from Japanese Patent Application No. 2017-109887, filed on Jun. 2, 2017.

TECHNICAL FIELD

The present invention relates to an agent for preventing or treating Alzheimer's disease, comprising 1-(3-(2-(1-benzothiophen-5-yl)ethoxy)propyl)azetidin-3-ol or a salt thereof as an active ingredient.

BACKGROUND ART

Dementia is a neurodegenerative disease with significantly reduced cognitive function caused by, for example, brain atrophy and/or cerebrovascular disorder. Dementia is classified into some types by its cause, and 60% to 80% of the patients with dementia suffers from Alzheimer's disease (AD) (Non Patent Literature 1). The pathogenesis of AD is complicated, and the cause is considered to be the formation of senile plaques due to coagulation of amyloid-β protein (Aβ) or neurofibrillary changes caused by coagulation of phosphorylated Tau protein (p-Tau) (Non Patent Literature 2). The number of patients with AD in Japan is estimated to be about more than 1,160,000. The incidence is higher in advanced age, and thus with the aging of society, the number of patients is expected to increase rapidly, causing a greater burden on patients' family and a sharp rise in medical and nursing care expenses in the future (Non Patent Literatures 3, 4). Thus, treatment of AD is important for not only preventing patients' quality of life from decreasing and reducing burden on their family thereafter, but also reducing medical expenses in the future aging society.

Symptoms of dementia include core symptoms of cognitive impairment and peripheral symptoms such as problem behaviors seen when patients with cognitive impairment interact with people around them (Non Patent Literature 5). At present four agents are used as an agent for treating AD in Japan: donepezil hydrochloride, galantamine hydrobromide, and rivastigmine, which are acetylcholinesterase inhibitors, and memantine hydrochloride which is a N-methyl-D-aspartate receptor antagonist. These are all capable of reducing core symptoms or peripheral symptoms. However, these drugs are symptomatic drugs which improve core symptoms or peripheral symptoms for a certain period of time, and do not suppress neurodegeneration in AD. Although these drugs are temporally effective in improving cognitive function at the beginning of use, the cognitive function usually becomes worse than cognitive function before the treatment, after about 48 weeks or more (Non Patent Literature 6).

1-(3-(2-(1-benzothiophen-5-yl)ethoxy)propyl)azetidin-3-ol (hereinafter referred to as "Compound A") or a salt thereof is known to have neuroprotective, nerve regeneration-promoting and neurite outgrowth actions, and be useful as a therapeutic agent for central and peripheral neurological diseases (Patent Literature 1). Furthermore, a publication discloses that usually the drug may be administered to an adult in a dose or divided doses of 0.01 to 500 mg per day (Patent Literature 2).

PRIOR ART LITERATURES

Patent Literature

Patent Literature 1: International Publication No. WO 2003/035647
Patent Literature 2: International Publication No. WO 2003/105830

Non-Patent Literature

Non Patent Literature 1: 2012 Alzheimer's Disease Facts and Figures, from the Alzheimer's Association.
Non Patent Literature 2: YAKUGAKU ZASSHI, 2010, Vol. 130, No. 4, pp. 521-526
Non Patent Literature 3: Japanese Journal of Clinical Medicine, 2008, Vol. 66 (Extra ed. 1), pp. 23-27
Non Patent Literature 4: Press Release by Seed Planning, Inc. of Japan, a market research company (Dec. 28, 2010)
Non Patent Literature 5: Japanese Journal of Clinical Psychopharmacology, 2011, Vol. 14, No. 7, pp. 1123-1129
Non Patent Literature 6: Japanese Journal of Clinical Psychopharmacology, 2012, Vol. 15, No. 3, pp. 311-321

SUMMARY OF INVENTION

Problem to be Solved by the Invention

Drugs which prevent progress of AD by inhibiting neurodegeneration need to be developed early. An object of the present invention is to provide a drug which prevents progress of AD and a method of preventing progress of AD.

Means for Solving Problem

In such circumstances, the present inventors have found that AD can be treated by initiating administration of Compound A or a salt thereof to a patient within a certain period from clinical diagnosis of AD, and the present invention has been completed.

The present invention provides the following.
(1) An agent for preventing or treating AD, comprising Compound A or a salt thereof as an active ingredient, wherein administration of the agent to a patient is initiated within 3.5 years from clinical diagnosis of AD.
(2) The agent for preventing or treating AD according to (1), wherein the patient is probable AD at clinical diagnosis of AD.
(3) The agent for preventing or treating AD according to (1), wherein the MMSE score of the patient is 12 or more at clinical diagnosis of AD.
(4) The agent for preventing or treating AD according to (1), wherein the patient has not received memantine.
(5) The agent for preventing or treating AD according to any one of (1) to (4), wherein the agent is orally administered once a day in a dose of 100 mg to 400 mg in terms of Compound A per administration.
(6) The agent for preventing or treating AD according to any one of (1) to (4), wherein the agent is orally administered once a day in a dose of 160 mg or 320 mg in terms of Compound A per administration.

The present invention also provides the following.
(a) A pharmaceutical composition for preventing or treating AD, comprising Compound A or a salt thereof, wherein administration of the pharmaceutical composition to a patient is initiated within 3.5 years from clinical diagnosis of AD.

(b) An agent for preventing or treating AD, comprising Compound A or a salt thereof, wherein the agent is for a patient within 3.5 years from clinical diagnosis of AD.

(c) Compound A or a salt thereof for use in prevention or treatment of AD, wherein administration of Compound A or a salt thereof to a patient is initiated within 3.5 years from clinical diagnosis of AD.

(d) A method of preventing or treating AD, comprising administering Compound A or a salt thereof, wherein the administration to a patient with AD is initiated within 3.5 years from clinical diagnosis of AD.

(e) Use of Compound A or a salt thereof for producing an agent for preventing or treating AD, wherein administration of Compound A or a salt thereof to a patient is initiated within 3.5 years from clinical diagnosis of AD.

(f) A method of assisting prediction of response to prevention or treatment comprising administration of Compound A or a salt thereof in a subject with a symptom of AD, the method comprising the steps of:

a. determining time of clinical diagnosis of AD of the subject; and b. predicting the response to the treatment in the subject based on the time of clinical diagnosis of AD, wherein a time within 3.5 years from clinical diagnosis of AD indicates that the response to the treatment in the subject is highly likely to be positive.

Advantageous Effects of Invention

AD can be prevented or treated by initiating administration of Compound A or a salt thereof to a patient within 3.5 years from clinical diagnosis of AD. Furthermore, reduction in patients' quality of life can be prevented, the burden of the family can be reduced and medical expenses can be reduced.

BRIEF DESCRIPTION OF DRAWINGS

FIG. 1 is a graph comparing the difference in mean changes of ADAS-cog from the baseline at week 52 in Test Example 1 between a high dose group and a placebo group and between a low dose group and the placebo group for patients who are around 2.6 years (median of all subject patients) from clinical diagnosis of AD.

FIG. 2 is a graph comparing the difference in mean changes of ADCS-ADL from the baseline at week 52 in Test Example 1 between the high dose group and the placebo group and between the low dose group and the placebo group for the patients who are around 2.6 years (median of all subject patients) from clinical diagnosis of AD.

FIG. 3 is a graph comparing the difference in mean changes of ADAS-cog from the baseline at week 52 in Test Example 2 between the low dose group and the placebo group for the patients who are around 2.6 years from clinical diagnosis of AD.

FIG. 4 is a graph comparing the difference in mean changes of ADCS-ADL from the baseline at week 52 in Test Example 2 between the low dose group and the placebo group for the patients who are around 2.6 years from clinical diagnosis of AD. (Test Example 2)

EMBODIMENTS FOR CARRYING OUT THE INVENTION

Hereinafter the present invention will be described in detail.

In the present description, the respective terms have the following meaning unless otherwise specified.

In the present description, the numerical range shown with "to" represents a range inclusive of the value before and after "to" as the minimum and maximum value, respectively.

Compound A means 1-(3-(2-(1-benzothiophen-5-yl)ethoxy)propyl)azetidin-3-ol.

Examples of salts of Compound A include known salts of a basic group such as amino group or an acidic group such as hydroxyl group or carboxyl group.

Examples of salts of a basic group include salts with a mineral acid such as hydrochloric acid, hydrogen bromide, nitric acid and sulfuric acid; salts with an organic carboxylic acid such as formic acid, acetic acid, citric acid, oxalic acid, fumaric acid, maleic acid, succinic acid, malic acid, tartaric acid, aspartic acid, trichloroacetic acid and trifluoroacetic acid; and salts with a sulfonic acid such as methanesulfonic acid, benzenesulfonic acid, p-toluenesulfonic acid, mesitylenesulfonic acid and naphthalenesulfonic acid.

Examples of salts of an acidic group include salts with an alkali metal such as sodium and potassium; salts with an alkaline earth metal such as calcium and magnesium; ammonium salts; and salts with a nitrogen-containing organic base such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-β-phenethylamine, 1-efenamin and N,N'-dibenzylethylenediamine.

Of the above salts, pharmacologically acceptable salts are preferred, and salts with maleic acid are more preferred.

In the case where Compound A or a salt thereof has isomers (e.g., optical isomers, geometric isomers and tautomers), the present invention includes all these isomers and also includes hydrates, solvates and any crystal forms thereof.

Prevention means to prevent the onset of a specific disease or at least one symptom caused by the disease.

Treatment means to reduce or improve at least one symptom caused by a specific disease with which a subject is affected, and delay the progress of the disease.

In an embodiment of the present invention, the term means, for example, to reduce or improve cognitive impairment or disturbed activities of daily living of a patient with AD, and delay the progress of cognitive impairment or disturbed activities of daily living. In the present description, "delay the progress of disease" means that development or aggravation of a disease in a treated subject is slower than those in a non-treated subject. For example, for AD, this delay can be determined by assessment using scales of cognitive functions (e.g., ADAS-cog, ADCS-ADL) based on the fact that negative change in a scale is slower in a treated subject than in a non-treated subject.

Clinical diagnosis of AD means to observe that a subject has developed AD, for example, by an interview with the subject, a neuropsychological test and an imaging test. For the clinical diagnosis of AD, Diagnostic and Statistical Manual of Mental Disorders, 4th edition, edited by the American Psychiatric Association, and the diagnostic criteria provided by the National Institute of Neurological and Communicative Disorders and Stroke/the Alzheimer's Disease and Related Disorders Associations (NINCDS-ADRDA) are recommended to be used. Furthermore, in 2011, new diagnostic criteria were proposed by the National Institute of Aging (NIA) and the Alzheimer Association (AA).

For AD, clinical diagnosis of "probable Alzheimer's disease" can be made according to the NINCDS-ADRDA diagnosis criteria.

A usual doctor may reasonably make clinical diagnosis of "mild to moderate Alzheimer's disease" using standard criteria. For example, according to the score of the standardized Mini-Mental State Examination (MMSE, scores of 0 to 30), clinical diagnosis of mild to moderate, moderate, or moderate to severe AD is provided. The MMSE (Folstein, Folstein and McHugh, 1975) is a simple test of cognitive function including an interview with patients. Orientation, memory, calculation and attention, language skills and other functions are assessed. The total score is 30. The lower the score, the higher the level of impairment of cognitive function.

In Test Examples of the present invention, patients with an MMSE score of 12 to 22 at the start of the test (screening) were determined as mild to moderate AD. Note that the MMSE is not the only way to clinically determine the grade of AD, though convenient.

Apolipoprotein E (ApoE), one of the apolipoproteins, constitutes lipoprotein and is involved in recognition of lipoprotein and lipid metabolism. ApoE has 3 isoforms of ApoE2, ApoE3 and ApoE4. A report shows that ApoE4 genotype encoding ApoE4 is correlated with the amount of deposition of amyloid-3 protein in the brain and the ApoE4 genotype is a risk gene of Alzheimer's disease.

The present invention is effective in prevention or treatment of all or part of the core symptoms or peripheral symptoms (BPSD) of AD. Core symptoms of AD include memory impairment, disorientation, executive function impairment, aphasia, agnosia and apraxia. Peripheral symptoms (BPSD) of AD include delusion, anxiety, insomnia, depression, wandering and delirium.

ADAS-cog (Rosen, Mobs, & Davis, 1984) is a standard for objective assessment of cognitive impairment which is a core symptom and is the most widely used method of assessment in clinical trials of AD. A total score is calculated from 11 items including word recall task, spoken language ability, comprehension of spoken language, word finding difficulty in spontaneous speech, following commands, naming objects and fingers, constructional praxis, ideational praxis, orientation, word recognition task and remembering test instructions. The score ranges from 0 to 70. The higher the score, the lower the cognitive function.

ADCS-ADL (Galasko et al. 1997) is a standard for activities of daily living. ADLs of a patient in the past 4 weeks are evaluated based on information from caregivers. The standard consists of 23 items of basic and instrumental ADLs. The score ranges from 0 to 78. The lower the score, the higher the level of impairment.

It is preferable that the patient to whom administration of Compound A or a salt thereof is initiated be at an early stage after developing AD or from clinical diagnosis of AD. More specifically, the patient is preferably within 3.5 years, within 3.4 years, within 3.3 years, within 3.2 years, within 3.1 years, within 3 years, within 2.9 years, within 2.8 years, within 2.7 years, within 2.6 years, more preferably within 3 years, and further preferably within 2.6 years from clinical diagnosis of AD. Furthermore, the patient is preferably within 3 years and 6 months, within 3 years and 5 months, within 3 years and 4 months, within 3 years and 3 months, within 3 years and 2 months, within 3 years and 1 month, within 3 years, within 2 years and 11 months, within 2 years and 10 months, within 2 years and 9 months, within 2 years and 8 months, within 2 years and 7 months, within 2 years and 6 months, more preferably within 3 years, and further preferably within 2 years and 7 months from clinical diagnosis of AD.

In many cases, patients have not received memantine within 2.6 years from clinical diagnosis of AD. Thus, in another embodiment, it is preferable that the patient to whom administration of Compound A or a salt thereof is initiated be a patient who has not received memantine. "Has not received memantine" means that the patient has not received treatment with memantine for 4 months before administration of Compound A or a salt thereof, or has not received treatment with memantine in a stable dose for 3 months before administration of Compound A or a salt thereof.

It is preferable that the time when administration of Compound A or a salt thereof is initiated be an early stage after developing AD or being clinically diagnosed as AD. More specifically, the patient is preferably within 3.5 years, within 3.4 years, within 3.3 years, within 3.2 years, within 3.1 years, within 3 years, within 2.9 years, within 2.8 years, within 2.7 years, within 2.6 years, more preferably within 3 years, and further preferably within 2.6 years from clinical diagnosis of AD. Furthermore, the patient is preferably within 3 years and 6 months, within 3 years and 5 months, within 3 years and 4 months, within 3 years and 3 months, within 3 years and 2 months, within 3 years and 1 month, within 3 years, within 2 years and 11 months, within 2 years and 10 months, within 2 years and 9 months, within 2 years and 8 months, within 2 years and 7 months, within 2 years and 6 months, more preferably within 3 years, and further preferably within 2 years and 7 months from clinical diagnosis of AD.

Compound A or a salt thereof used in the present invention may be prepared by a method known per se or by combining such methods, or by the method disclosed in Patent Literature 1.

Compound A or a salt thereof used in the present invention may be blended with various pharmaceutical additives such as an excipient, a binding agent, a disintegrating agent, a disintegration inhibitor, a consolidation/adhesion-preventing agent, a lubricant, an absorption/adsorption carrier, a solvent, a bulking agent, an isotonic agent, a solubilizer, an emulsifier, a suspending agent, a thickener, a coating agent, an absorption enhancer, a gelling/procoagulant agent, a light stabilizer, a preservative, a desiccant, an emulsification/suspension/dispersion stabilizer, a color protecting agent, a deoxidant/antioxidant, a flavoring agent, a coloring agent, a foaming agent, an antifoaming agent, a soothing agent, an antistatic agent, a buffer, and/or a pH adjuster to give a pharmaceutical preparation such as an oral preparation (e.g., tablets, capsules, powders, granules, fine granules, pills, suspensions, emulsions, liquids, and syrups), injections, eye drops, nasal sprays and transdermal agents. Tablets are preferred as an oral dosage form for patients with AD.

The above agents are formulated by a usual method.

The method of administration of Compound A, which is not particularly limited, is accordingly determined based on the form of the preparation, the age, sex and other conditions of the patient and the level of symptoms of the patient.

The dose of Compound A is accordingly selected based on the administration, the age, sex, type of disease and other conditions of the patient.

The agent may be administered to an adult in a dose or divided doses of usually 40 to 500 mg in terms of Compound A per day. The agent is administered in a dose or divided doses of preferably 100 to 400 mg in terms of Compound A per day, and administered in a dose of further preferably 160 mg or 320 mg in terms of Compound A per day.

In the administration of Compound A or a salt thereof in the present invention, prevention or treatment by administration of acetylcholinesterase inhibitors (AChEIs) may also be included. Examples of AchEIs include donepezil hydrochloride, galantamine hydrochloride, rivastigmine tartrate and tacrine hydrochloride.

In the present invention, the subject may have undergone prevention or treatment by administration of AChEI for at least 6 months before administration of Compound A or a salt thereof.

Next, the present invention will be described with reference to Test Examples and Preparation Examples, but the present invention is not limited thereto.

Maleate of Compound A was used as the test compound.

Test Example 1 Multicenter Randomized Double-Blind Phase II Placebo-Controlled Trial for Assessing Effectiveness and Safety of Compound a in Mild to Moderate AD Patients Patients were screened in a period from 42 days before treatment assignment to the assignment based on the following selection criteria. Patients matched (484 patients) were randomly divided into the following 3 groups and the trial was started.

Subject (Selection Criteria):
- Patients who were probable AD and are 55 years old or older and 85 years old or younger at the time of obtaining consent of screening.
- Patients with an MMSE score of 12 to 22 at the time of screening
- Patients with a Modified Hachinski Ischemia Scale score of 4 or less
- Patients who have been treated with a donepezil hydrochloride or rivastigmine transdermal system for at least 4 months before the baseline and with a stable dose thereof for 3 months before the baseline.
- In the case of patients who have received memantine in addition to being treated with a donepezil hydrochloride or rivastigmine transdermal system, patients who have been treated with memantine for at least 4 months before the baseline and with a stable dose thereof for 3 months before the baseline.
- Patients whose brain MRI or CT results match AD at the time of screening Organization of Groups:
(1) High dose group: 224 mg of a test compound (160 mg in terms of Compound A) was orally administered once a day for 4 weeks and then 448 mg of a test compound (320 mg in terms of Compound A) was orally administered once a day for 48 weeks (158 patients)
(2) Low dose group: 224 mg of a test compound (160 mg in terms of Compound A) was orally administered once a day for 52 weeks (166 patients)
(3) Placebo group: placebo was orally administered once a day for 52 weeks (158 patients) Method of assessment:
(1) ADAS-cog
 The ADAS-cog score of the subject was evaluated at the baseline (before administration of investigational drug on the first day of administration) and after 52 weeks and the cognitive function was assessed based on the change from the baseline.
(2) ADCS-ADL
 The ADCS-ADL score of the subject was evaluated at the baseline (before administration of investigational drug on the first day of administration) and after 52 weeks and the level of impairment was assessed based on the change from the baseline.

Statistical Analysis:
 Changes in the ADAS-cog score and the ADCS-ADL score after 52 weeks from the baseline were compared between the high dose group and the placebo group, and between the low dose group and the placebo group based on the Mixed-effect Models for Repeated Measures (MMRM) with a significance level of 5%. For models, fixed effects included the treatment groups and time, while covariates included age, the baseline of ADAS-cog or ADCS-ADL, the baseline of MMSE and ApoE4 genotype (positive/negative). The interaction between time and the treatment groups and the interaction between the baseline of ADAS-cog and time were also included.

Results: shown below
(1) Changes in ADAS-cog from the baseline at week 52 are shown in Table 1, Table 2 and FIG. 1. The "number of cases" in Table 1 and Table 2 means the number of patients used as models until week 52 including withdrawals.

TABLE 1

| Group | Number of cases/statistics | Period from clinical diagnosis | | |
| --- | --- | --- | --- | --- |
| | | Within 2.6 years | More than 2.6 years | Total |
| high dose group | Number of cases | 79 | 74 | 153 |
| | Least square means (95% Confidence interval)) | 5.8(3.9, 7.8) | 8.4(6.3, 10.5) | 7.1(5.6, 8.6) |
| | Difference from placebo group (95% Confidence interval) | −3.1(−5.7, −0.5) | 1.8(−1.0, 4.6) | −0.8(−2.7, 1.1) |
| | p-value | 0.018 | 0.215 | 0.392 |
| low dose group | Number of cases | 71 | 87 | 158 |
| | Least square means (95% Confidence interval) | 8.1 (6.0, 10.2) | 6.8 (4.8, 8.7) | 7.4 (6.0, 8.9) |
| | Difference from placebo group (95% Confidence interval) | −0.9 (−3.6, 1.8) | 0.1 (−2.5, 2.8) | −0.5 (−2.4, 1.4) |
| | p-value | 0.526 | 0.929 | 0.631 |
| placebo group | Number of cases | 81 | 74 | 155 |
| | Least square means (95% Confidence interval) | 9.0 (7.1, 10.9) | 6.6 (4.7, 8.6) | 7.9 (6.5, 9.3) |

TABLE 2

| Group | Number of cases/statistics | Period from clinical diagnosis | | | | | |
|---|---|---|---|---|---|---|---|
| | | Within 2.5 years | Within 2.6 years | Within 2.8 years | Within 3 years | Within 3.2 years | Within 3.4 years |
| High dose group | Number of cases | 75 | 79 | 84 | 93 | 98 | 103 |
| | Least square means | 5.6 | 5.8 | 6.2 | 6.1 | 6.4 | 6.4 |
| | (95% Confidence interval) | (3.6, 7.6) | (3.9, 7.8) | (4.3, 8.1) | (4.4, 8.1) | (4.6, 8.3) | (4.6, 8.2) |
| | Difference from placebo group | −3.3 | −3.1 | −2.5 | −2.2 | −2.0 | −1.8 |
| | (95% Confidence interval) | (−5.9, −0.6) | (−5.7, −0.5) | (−5.0, 0.0) | (−4.7, 0.2) | (−4.4, 0.4) | (−4.1, 0.5) |
| | p-value | 0.015 | 0.018 | 0.054 | 0.073 | 0.096 | 0.122 |
| Placebo group | Number of cases | 80 | 81 | 90 | 96 | 104 | 109 |
| | Least square means | 8.9 | 9.0 | 8.7 | 8.5 | 8.4 | 8.7 |
| | (95% Confidence interval) | (7.0, 10.8) | (7.1, 10.9) | (6.8, 10.5) | (6.7, 10.3) | (6.7, 10.1) | (6.6, 9.9) |

| Group | Number of cases/statistics | Period from clinical diagnosis | | | | | |
|---|---|---|---|---|---|---|---|
| | | Within 3.6 years | Within 3.8 years | Within 4.0 years | Within 5.0 years | Within 6.0 years | Total |
| High dose group | Number of cases | 108 | 115 | 121 | 132 | 145 | 153 |
| | Least square means | 6.7 | 6.5 | 6.6 | 6.5 | 7.2 | 7.1 |
| | (95% Confidence interval) | (5.0, 8.5) | (4.8, 8.2) | (5.0, 8.3) | (4.9, 8.1) | (5.7, 8.8) | (5.6, 8.6) |
| | Difference from placebo group | −1.8 | −2.1 | −1.7 | −1.9 | −0.9 | −0.8 |
| | (95% Confidence interval) | (−4.1, 0.4) | (−4.3, 0.1) | (−3.9, 0.4) | (−3.9, 0.1) | (−2.9, 1.0) | (−2.7, 1.1) |
| | p-value | 0.108 | 0.057 | 0.116 | 0.068 | 0.352 | 0.392 |
| Placebo group) | Number of cases | 114 | 120 | 123 | 135 | 142 | 155 |
| | Least square means | 8.6 | 8.6 | 8.3 | 8.4 | 8.7 | 7.9 |
| | (95% Confidence interval) | (6.9, 10.2) | (7.0, 10.2) | (6.8, 9.9) | (6.9, 9.9) | (6.7, 9.7) | (6.5, 9.3) |

For the changes in ADAS-cog from the baseline at week 52, there was no statistically significant difference for all subject patients in the Compound A group and the placebo group. In contrast, there was a statistically significant difference between the Compound A high dose group and the placebo group for the subject patients who were within 2.6 years (median of all subject patients) from clinical diagnosis of AD. Furthermore, in the Compound A low dose group, decrease in the ADAS-cog score tended to be smaller than that in the placebo group. A comparison of results by periods from clinical diagnosis of AD (2.5 to 6 years) has revealed that the difference between the Compound A high dose group and the placebo group was larger in patients whose period was shorter.

(2) Changes in ADCS-ADL from the baseline at week 52 are shown in Table 3 and FIG. 2. The "number of cases" in Table 3 means the number of patients used as models until week 52 including withdrawals.

TABLE 3

| Group | Number of cases/statistics | Period from clinical diagnosis | | |
|---|---|---|---|---|
| | | Within 2.6 years | More than 2.6 years | Total |
| High dose group | Number of cases | 79 | 74 | 153 |
| | Least square means (95% Confidence interval) | −8.6(−11.2, −5.9) | −11.6(−14.5, −8.8) | −10.1(−12.0, −8.1) |
| | Difference from placebo group (95% Confidence interval) | 3.1(−0.4, 6.6) | −0.9 (−4.7, 2.8) | 1.2(−1.3, 3.8) |
| | p-value | 0.079 | 0.627 | 0.352 |
| Low dose group | Number of cases | 72 | 87 | 159 |
| | Least square means (95% Confidence interval) | −11.7(−14.5, −9.0) | −10.4(−13.0, −7.8) | −11.0(−13.0, −9.1) |
| | Difference from placebo group (95% Confidence interval) | 0.0(−3.6, 3.6) | 0.3(−3.2, 3.8) | 0.2(−2.3, 2.7) |
| | p-value | 0.989 | 0.864 | 0.861 |
| Placebo group | Number of cases | 81 | 75 | 156 |
| | Least square means (95% Confidence interval) | −11.7(−14.2, −9.2) | −10.7(−13.3, −8.1) | −11.3(−13.1, −9.4) |

For the changes in ADCS-ADL from the baseline at week 52, reduction in ADCS-ADL tended to be suppressed in the Compound A high dose group. This tendency was more remarkable when the subject was the patients who were within 2.6 years (median of all subject patients) from clinical diagnosis of AD than when the subject was all patients.

Test Example 2 Multicenter Randomized Double-Blind Early Phase II Placebo-Controlled Trial for Assessing Effectiveness and Safety of Compound a in Mild to Moderate AD Patients Patients were screened in a period from 28 days before treatment assignment to the assignment based on the following selection criteria. Patients matched (373 patients) were randomly divided into the following 2 groups and the trial was started.

Subject (Selection Criteria):
  Patients who were probable AD and over or 50 years old or older and 90 years old or younger at the time of obtaining consent of screening.
  Patients with an MMSE score of 15 to 24 at the time of screening
  Patients with a Modified Hachinski Ischemia Scale score of 4 or less
  Patients who have been treated with a donepezil hydrochloride for at least 6 months before the baseline and with a stable dose thereof for 3 months before the baseline.
  Patients whose brain MRI or CT results match AD at the time of screening Organization of Groups:
(1) Active drug group: 224 mg of a test compound (160 mg in terms of Compound A) was orally administered once a day for 52 weeks (176 patients)
(2) Placebo group: placebo was orally administered once a day for 52 weeks (178 patients) Method of assessment:
(1) ADAS-cog
  The ADAS-cog score of the subject was evaluated at the baseline (before administration of investigational drug on the first day of administration) and after 52 weeks and the cognitive function was assessed based on the change from the baseline.
(2) ADCS-ADL
  The ADCS-ADL score of the subject was evaluated at the baseline (before administration of investigational drug on the first day of administration) and after 52 weeks and the level of impairment was assessed based on the change from the baseline.

Statistical Analysis:
  Changes in the ADAS-cog score and the ADCS-ADL score after 52 weeks from the baseline were compared between the high dose group and the placebo group, and between the low dose group and the placebo group based on MMRM with a significance level of 5%. For models, fixed effects included the treatment groups and time, while covariates included the baseline of ADAS-cog or ADCS-ADL and the baseline of MMSE. The interaction between time and the treatment groups and the interaction between the baseline of ADAS-cog and time were also included. For the period from clinical diagnosis, the first day of administration of donepezil hydrochloride which was combined with Compound A was defined as the time of clinical diagnosis. Furthermore, to match the conditions with those of Test Example 1, the subject was patients with an MMSE score of 22 or less at the time of screening.

Results: shown below
(1) Changes in ADAS-cog from the baseline at week 52 are shown in Table 4. The "number of cases" in Table 4 means the number of patients used as models until week 52 including withdrawals.

TABLE 4

| Group | Number of cases/statistics | Period from clinical diagnosis | | |
|---|---|---|---|---|
| | | Within 2.6 years | More than 2.6 years | Total |
| Low dose group | Number of cases | 70 | 42 | 112 |
| | Least square means (95% Confidence interval) | 1.3(−0.3, 4.7) | 3.0(0.8, 5.3) | 1.9(0.5, 3.2) |
| | Difference from placebo group (95% Confidence interval) | −2.6(−4.8, −0.5) | 1.7(−1.3, 4.7) | −1.2(−3.0, 0.5) |
| | p-value | 0.017 | 0.268 | 0.167 |
| Placebo group | Number of cases | 70 | 37 | 107 |
| | Least square means (95% Confidence interval) | 3.9(2.3, 5.5) | 1.3(−0.3, 2.9) | 3.1(1.8, 4.4) |

For the changes in ADAS-cog from the baseline at week 52, there was no statistically significant difference for all subject patients in the Compound A group and the placebo group. In contrast, there was a statistically significant difference between the Compound A low dose group and the placebo group for the subject patients who were within 2.6 years from clinical diagnosis of AD and with an MMSE score of 22 or less at the time of screening (same condition as in Test Example 1).

(2) Changes in ADCS-ADL from the baseline at week 52 are shown in Table 5. The "number of cases" in Table 5 means the number of patients used as models until week 52 including withdrawals.

TABLE 5

| Group | Number of cases/statistics | Period from clinical diagnosis | | |
|---|---|---|---|---|
| | | Within 2.6 years | More than 2.6 | Total |
| Low dose group | Number of cases | 72 | 44 | 116 |
| | Least square means (95% Confidence interval) | −5.5(−7.8, −3.2) | −7.5(−10.8, −4.3) | −6.2(−8,1, −4.3) |
| | Difference from placebo group (95% Confidence interval) | 2.6(−0.5, 5.7) | −3.5(−7.8, 0.8) | 0.5(−2.0, 3.0) |
| | p-value | 0.103 | 0.115 | 0.686 |
| Placebo group | Number of cases | 70 | 37 | 107 |
| | Least square means (95% Confidence interval) | −8.1(−10.3, −5.8) | −4.1(−7.3, −0.9) | −6.7(−8.6, −4.8) |

For the changes in ADCS-ADL from the baseline at week 52, reduction in ADCS-ADL tended to be suppressed in the Compound A low dose group. This tendency was more remarkable when the subject was the patients who were within 2.6 years from clinical diagnosis of AD than when the subject was all patients.

Preparation Example 1

0.9726 g of magnesium stearate (magnesium stearate, Merck) was added to 174.03 g of maleate of Compound A and the mixture was mixed for 30 minutes. The mixed powder was compression-molded by a roller compactor (TF-LABO (roll pressure 3 MPa), Freund Corporation), and the solid obtained by molding was granulated. 49.51 g of lactose (FlowLac 90, Meggle Japan), 16.50 g of crystalline cellulose (CEOLUS PH302, Asahi Kasei Chemicals) and 6.67 g of croscarmellose sodium (Primellose, DMV Japan) were each sieved through a sieve with an opening of 850 μm and added to 60.0 g of the resulting granulated powder, and the mixture was mixed for 10 minutes. 0.6667 g of magnesium stearate was added to the mixed powder and the mixture was mixed for 30 minutes. The mixed powder was tableted by a tableting machine (HT-P18A, Hata Tekkosho) at a tableting pressure of about 12 kN using a pestle having a double rounded surface with a tablet diameter of 8.5 mm to obtain round uncoated tablets each weighing 250 mg. The uncoated tablets were coated with 8 mg of a coating agent per tablet using a film coater DRC-200 (Powrex), and then a small amount of carnauba wax (Polishing Wax-105, Nippon Wax) was added thereto to give film-coated tablets.

Preparation Example 2

60.90 g of mannitol (Parteck M200, Merck) and 3.60 g croscarmellose sodium were added to 53.70 g of maleate of Compound A and the mixture was mixed for 10 minutes. 1.80 g of magnesium stearate was added to the mixed powder and the mixture was mixed for 30 minutes. The mixed powder was tableted at a tableting pressure of about 10 kN using a pestle having a double rounded surface with a tablet diameter of 8.5 mm to obtain round uncoated tablets each weighing 250 mg. The uncoated tablets were coated with 8 mg of a coating agent (Opadry 03F44057, 00F440000 (hypromellose 2910: 71.5%, Macrogol 6000: 14.166%, talc: 7.167%, titanium oxide: 7.067%, iron sesquioxide: 0.1%), Colorcon Japan LLC) per tablet, and then a small amount of carnauba wax was added thereto to give film-coated tablets.

Preparation Example 3

11.11 g of magnesium stearate was added to 1988.89 g of maleate of Compound A and the mixture was mixed for 30 minutes. The mixed powder was compression-molded by a roller compactor, and the solid obtained by molding was granulated. To 107.13 g of the resulting granulated powder were added 26.21 g of mannitol, 7.50 g of ethyl cellulose (ETHOCEL 100FP Premium, The Dow Chemical Company), 3.75 g of crystalline cellulose (CEOLUS KG-1000, Asahi Kasei Chemicals), 3.75 g of crospovidone (Kollidon CL-SF, BASF) and 0.75 g of croscarmellose sodium, and the mixture was mixed for 30 minutes. 0.90 g of magnesium stearate was added to the mixed powder and the mixture was mixed for 5 minutes. The mixed powder was tableted at a tableting pressure of about 7 kN using a pestle having a double rounded surface with a tablet diameter of 8.5 mm to obtain round uncoated tablets each weighing 315 mg. The uncoated tablets were coated with 9 mg of a coating agent per tablet, and then a small amount of carnauba wax was added thereto to give film-coated tablets.

The invention claimed is:

1. A method of preventing or treating Alzheimer's disease, comprising administering 1-(3-(2-(1-benzothiophen-5-yl)ethoxy)propyl)azetidin-3-ol or a salt thereof, wherein the administration to a patient with Alzheimer's disease is initiated within 3.5 years from clinical diagnosis of Alzheimer's disease.

2. The method for preventing or treating Alzheimer's disease according to claim 1, wherein the patient is probable Alzheimer's disease at clinical diagnosis of Alzheimer's disease.

3. The method for preventing or treating Alzheimer's disease according to claim 1, wherein the MMSE score of the patient is 12 or more at clinical diagnosis of Alzheimer's disease.

4. The method for preventing or treating Alzheimer's disease according to claim 1, wherein the patient has not received memantine.

5. The method for preventing or treating Alzheimer's disease according to claim 1, wherein 1-(3-(2-(1-benzothiophen-5-yl)ethoxy)propyl)azetidin-3-ol or a salt thereof is orally administered once a day in a dose of 100 mg to 400 mg in terms of 1-(3-(2-(1-benzothiophen-5-yl)ethoxy)propyl)azetidin-3-ol per administration.

6. The method for preventing or treating Alzheimer's disease according to claim 1, wherein 1-(3-(2-(1-benzothiophen-5-yl)ethoxy)propyl)azetidin-3-ol or a salt thereof is orally administered once a day in a dose of 160 mg or 320 mg in terms of 1-(3-(2-(1-benzothiophen-5-yl)ethoxy)propyl)azetidin-3-ol per administration.

* * * * *